United States Patent [19]

Petersen

[11] Patent Number: 4,907,578
[45] Date of Patent: * Mar. 13, 1990

[54] METHOD AND INSTRUMENTS FOR RESECTION OF THE DISTAL FEMUR

[76] Inventor: Thomas D. Petersen, 555 Reservoir Dr., San Diego, Calif. 92120

[*] Notice: The portion of the term of this patent subsequent to Sep. 27, 2005 has been disclaimed.

[21] Appl. No.: 247,495

[22] Filed: Sep. 22, 1988

Related U.S. Application Data

[63] Continuation-in-part of Ser. No. 888,525, Jul. 23, 1986, Pat. No. 4,775,407.

[51] Int. Cl.⁴ .............................................. A61B 17/56
[52] U.S. Cl. .......................................... 606/79; 606/88
[58] Field of Search ......... 128/92 VW, 92 VY, 92 V, 128/92 R

[56] References Cited

U.S. PATENT DOCUMENTS

| | | | |
|---|---|---|---|
| 4,457,307 | 7/1984 | Stillwell | 128/92 VW |
| 4,474,177 | 10/1984 | Whiteside | 128/92 VW |
| 4,487,203 | 12/1984 | Androphy | 128/92 VW |
| 4,502,483 | 3/1985 | Lacey | 128/92 VW |
| 4,524,766 | 6/1985 | Peterson | 128/92 VW |
| 4,567,885 | 2/1986 | Androphy | 128/92 VW |
| 4,646,429 | 3/1987 | Kenna et al. | 128/92 VW |
| 4,653,488 | 3/1987 | Kenna et al. | 128/92 VW |
| 4,703,751 | 11/1987 | Pohl | 128/92 VW |

Primary Examiner—Robert A. Hafer
Assistant Examiner—Kevin G. Rooney
Attorney, Agent, or Firm—H. Jay Spiegel

[57] ABSTRACT

The present invention relates to an improved method and instruments for a resection of the distal femur. The parent application discloses a femoral alignment guide/-rod including a plate insertable within a guide slot in the resector which is also used for the guided insertion of a cutting tool. The present invention improves upon this structure by providing an auxiliary attachment member on the resector allowing attachment of a new femoral alignment guide/rod on the resector housing proximal to the cutting tool guide slot, which new guide/rod allows easier access to various resector components. In a further aspect, structure is provided allowing the use of the resector with an intramedullary rod to increase accuracy. In this aspect, a gauge is incorporated in the resector which allows compensation for the angle between the mechanical axis of the leg and the longitudinal extent of the internal cavity of the femur while also allowing compensation or correction for specific anatomical conditions such as, for example, valgus correction.

32 Claims, 4 Drawing Sheets

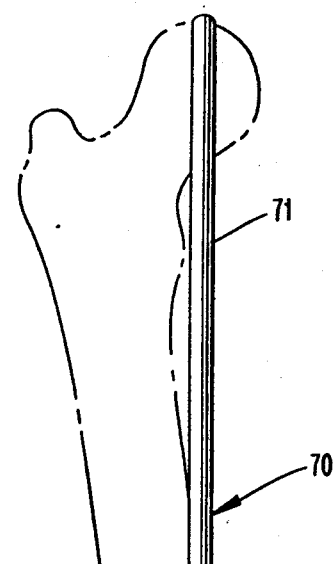
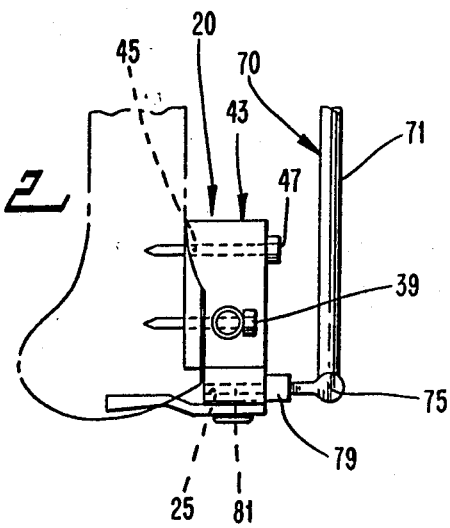
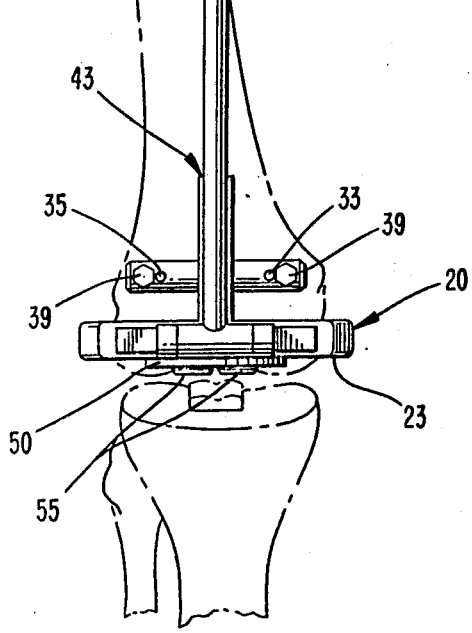
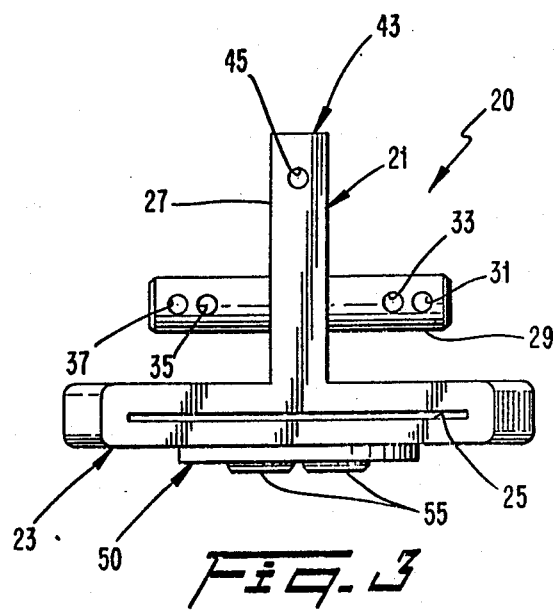

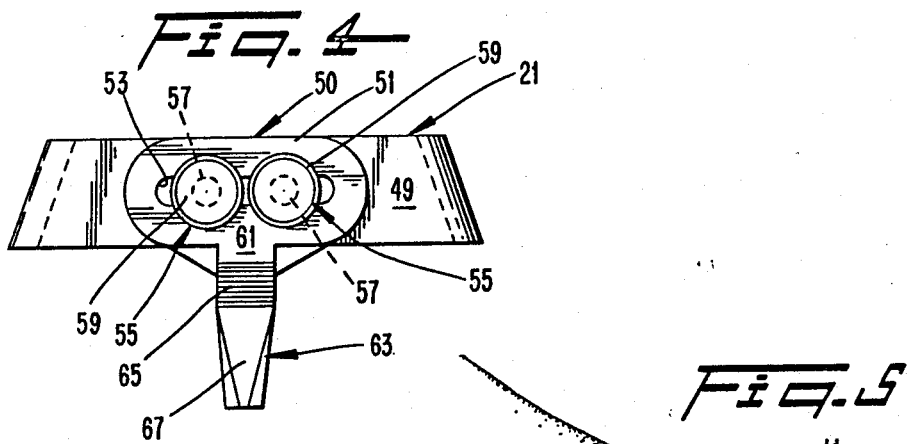
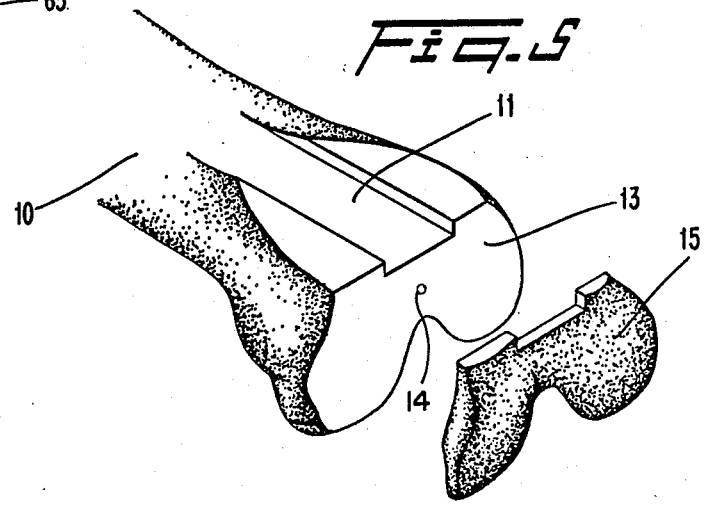
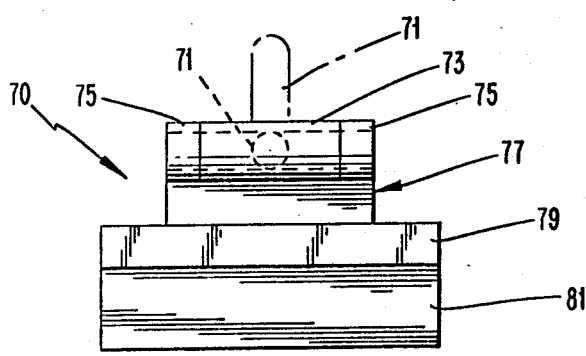
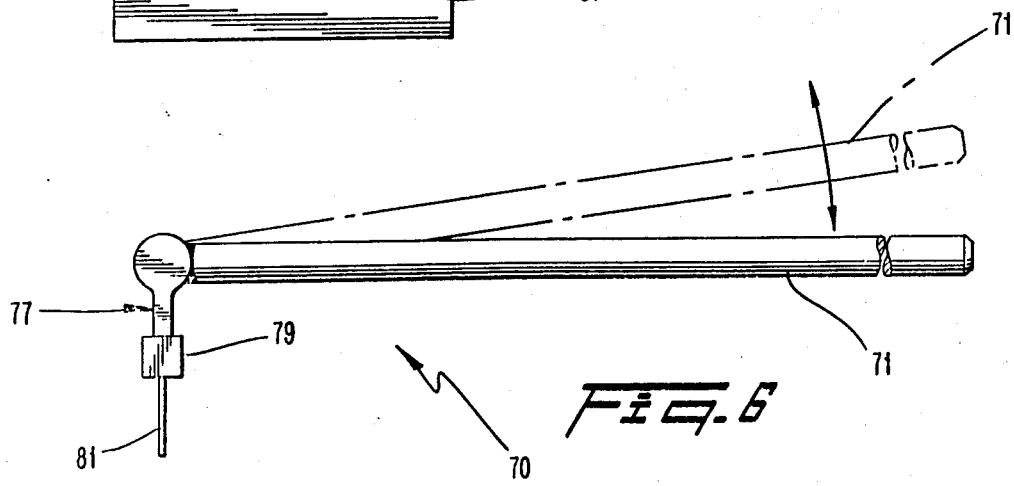

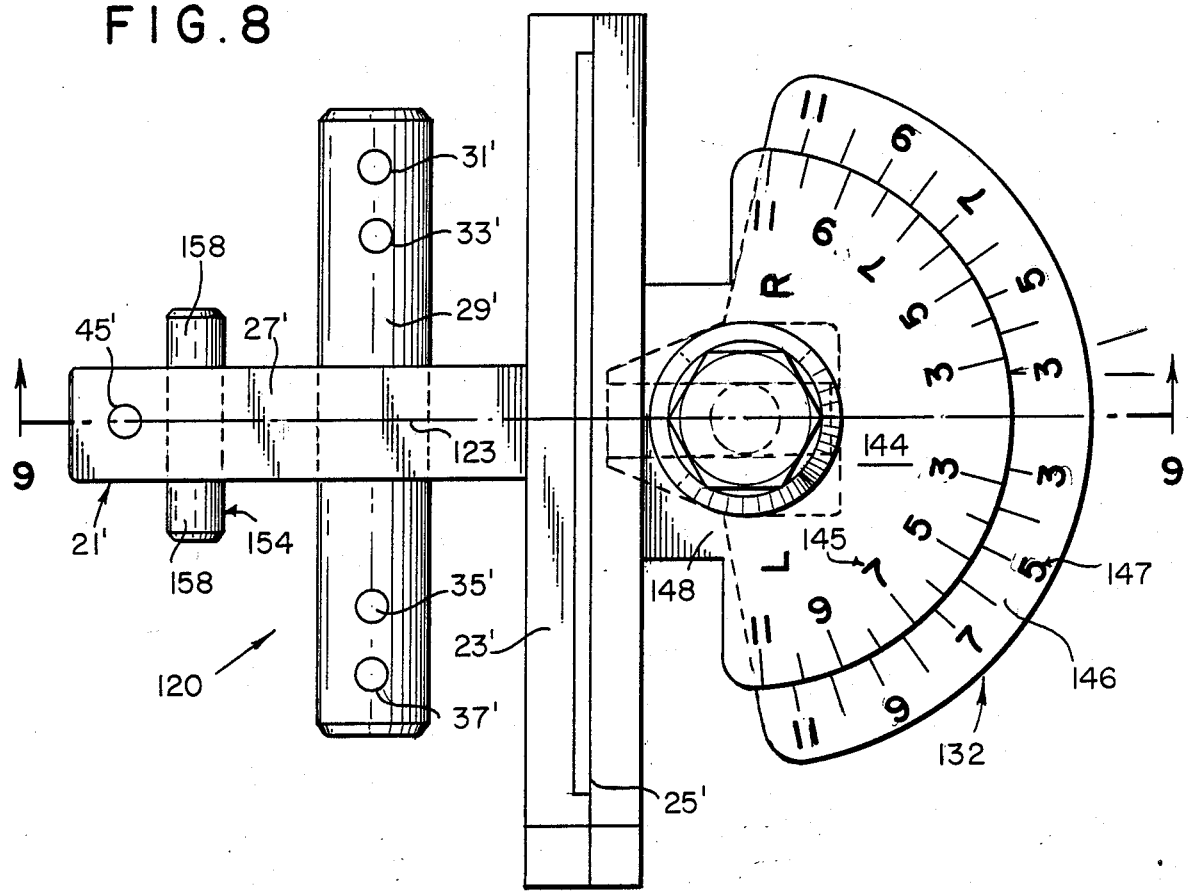
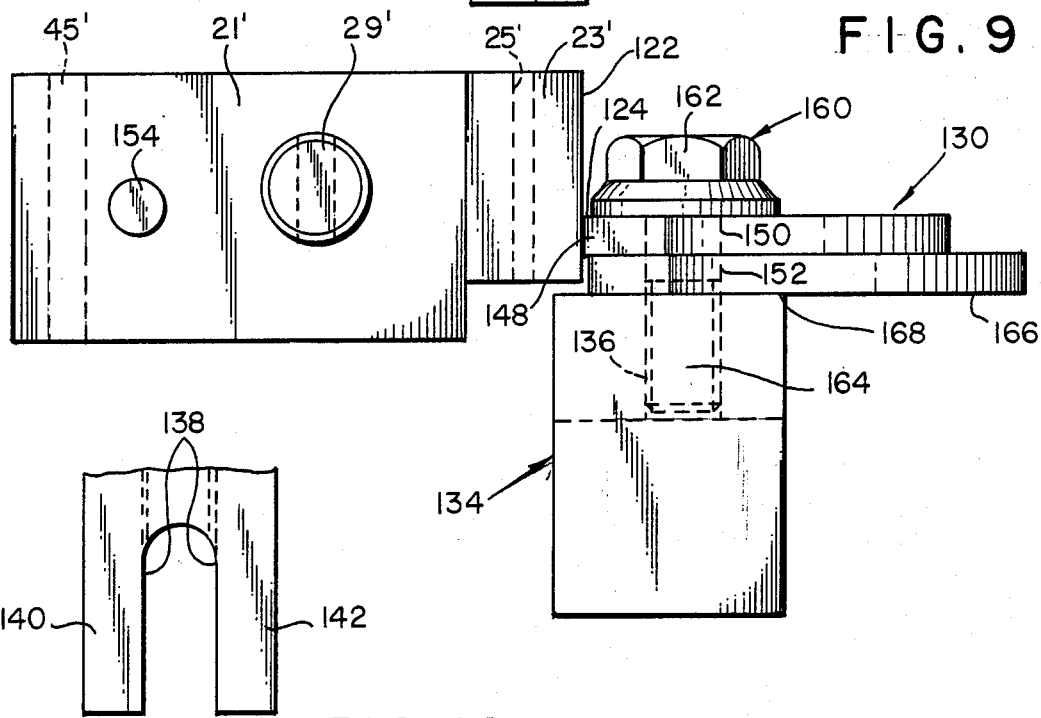

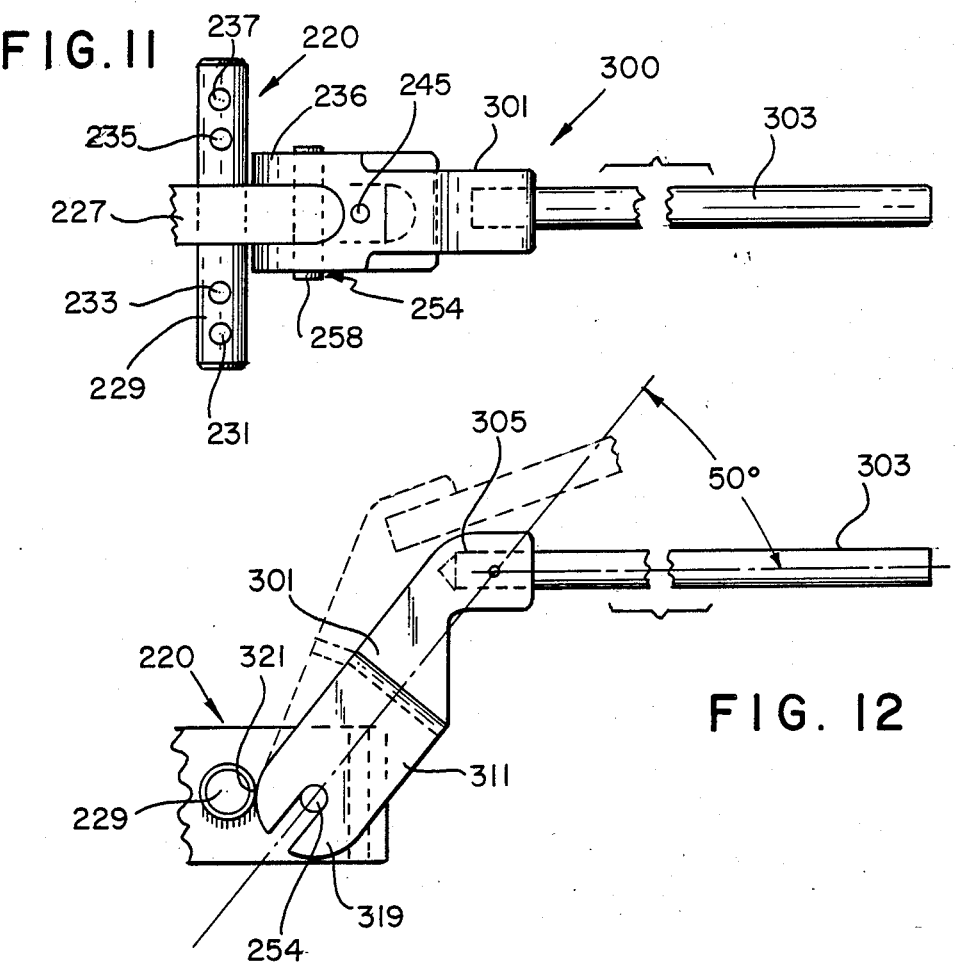
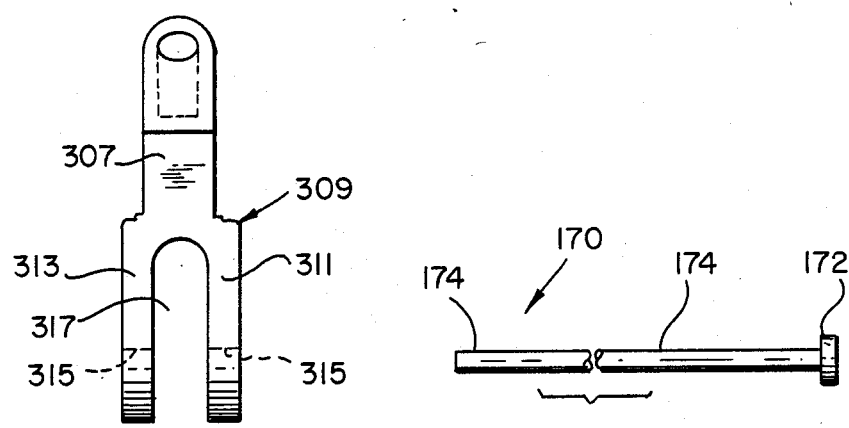

METHOD AND INSTRUMENTS FOR RESECTION OF THE DISTAL FEMUR

BACKGROUND AND SUMMARY OF THE INVENTION

This application is a continuation in part of U.S. patent application Ser. No. 06/888,525, filed July 23, 1986 now U.S. Pat. No. 4,773,407 issued Sept. 27, 1988. Application Ser. No. 06/888,525 is incorporated in its entirety by reference herein.

In the parent application, method and instruments for resection of the distal femur are disclosed. The instruments disclosed include a distal femoral resector having a T-shaped configuration with the base of the "T" having a rotating rod extending normally therethrough, which rotating rod allows fixation of the resector while allowing the resector to be placed flush against a plane filed on the anterior femoral cortex.

Also disclosed in the parent application is a femoral alignment guide/rod which includes a plate insertable into a cutting tool guide slot in the distally-located top of the "T", which guide/rod includes an elongated pivoting rod designed to be pivotable to a position overlying the femoral head of the femur to allow determination of the mechanical axis of the leg.

In a further aspect, the resector disclosed in the parent application includes a feeler gauge laterally-adjustable to allow adaptation to the intercondylar notch of the particular patient to allow centering of the resector with respect to a centrally-located anatomical landmark on the patient's knee. A further reason for the use of the feeler gauge is to define in the proximal to distal direction the location of the guide slot and therefore of the cut which will be carried out on the distal femur with respect to the particular location of the particular intercondylar notch of the particular patient.

Applicant has used the instruments disclosed in the parent application in performing surgery on numerous patients to provide these patients with artificial knee prostheses. While these operations have been universally successful, in some minor and subtle respects, the specific design of the instruments disclosed in the parent application has led to slight surgical complications.

Thus, the design of the femoral alignment guide/rod including a plate 81 designed to be inserted within the slot 25 of the resector housing 21 causes the rod portion 71 of the guide/rod to extend distally of the rotating rod 29 which rod is essential in allowing the resector housing 21 to be installed on the planar surface which has been filed on the anterior femoral cortex in flush relation thereto. Thus, the use of the cutting slot 25 to mount the guide/rod causes two problems. Firstly, such mounting prevents the surgeon from being able to look through the cutting slot 25 during alignment of the housing 21 to facilitate "eyeballing" of the portion of the distal femur which is to be cut. Furthermore, the fact that the distal portion of the rod 71 of the guide/rod 70 overlies the rotating rod 29 makes it difficult to drive pins through the openings 31, 33, 35 and 37 of the rotating rod 29 when fixating the resector housing 21 on the planer surface which has been formed on the anterior femoral cortex.

These problems with the location of detachable mounting of the guide/rod have caused minor complications during surgery which increased the length of time necessary in performing such surgery. Thus, Applicant has recognized the need to provide a guide/rod which may be mounted to the resector housing 21 with the same angular relationship thereto as is the case with the guide/rod 70 disclosed in the parent application, while eliminating the problems associated with the guide/rod 70 as described hereinabove.

In a further aspect, the operation of the instruments disclosed in the parent application is extramedullary in nature. In particular, the method disclosed in the parent application of carrying out surgery using the instruments disclosed therein is relatively non-invasive. Applicant has discovered through careful experimentation that the instrument disclosed in the parent application may be modified to allow an intramedullary approach which increases the accuracy of the resections which must be carried out in preparing the distal femur for the installation of a distal femoral prosthesis. The common thread which may be found between the instruments disclosed in the parent application and the instruments disclosed herein is the use of a centrally-located anatomical landmark to perform calculations and measurements to determine precisely where resections are to take place. This anatomical landmark is the intercondylar notch as described hereinabove.

Applicant has discovered that the use of the instruments disclosed in the parent application with modifications thereto to allow an intramedullary technique vastly increases the accuracy of the resections to the extent that accuracy to within 25° is achievable, as compared to the 3°-5° error which may sometimes occur through the use of prior art instruments and techniques.

In this aspect, the distal femoral resector disclosed in the parent application is modified through replacement of the laterally-adjustable intercondylar notch pin with a slotted centrally-located notch block with a protractor device having two scales which may be selectively aligned to define the angular relationship between the resector and the mechanical axis of the leg on the one hand and the direction of longitudinal extent of the canal within the femur which contains marrow on the other hand. The protractor device may additionally be used to dial in any desired correction, as anatomical deformity may dictate.

Located below the protractor device is a slotted locator designed to be easily slid over the distal end of an elongated rod designed to be inserted into the intramedullary canal after a small hole has been drilled through the intercondylar notch. As will be described in greater detail hereinafter, the greater the length of the elongated rod, the greater the accuracy of the technique.

In using the intramedullary technique, a single X-ray is taken of the leg to determine the angular relationship between the mechanical axis of the leg and the direction of elongation of the intramedullary canal of the femur. This angle is dialed into the protractor device and, if desired, the angle dialed into the protractor device may be additionally modified to provide correction for anatomical conditions such as, for example, valgus condition. With the protractor device being set in this manner, a small hole is drilled through the intercondylar notch and the intramedullary rod is inserted through the hole and all the way into the intramedullary canal so that only a small portion of the rod extends distally of the intercondylar notch. Thereafter, the resector device may be placed on a plane formed on the anterior femoral cortex, with the slot under the protractor device being placed over the distal end of the intramedullary rod. In this way, the angular relationship of the resector with respect to an axis of rotation thereof perpendicular to the longitudinal extent of the femur may be precisely determined to allow for placement of the angular relationship between the cutting slot of the resector and the distal femur to within less than ¼°. The use of the anatomical landmark, to wit, the intercondylar notch, allows such accuracy to be a reality.

Accordingly, it is a first object of the present invention to provide an improved method and instruments for resection of the distal femur.

It is a further object of the present invention to provide improved instruments which include distal interconnection between the resector housing and the femoral alignment guide/rod.

It is a yet further object of the present invention to provide a distal femoral resector which may be used with an intramedullary surgical technique.

These and other objects, aspects and features of the present invention will be better understood from the following detailed description of the preferred embodiments when read in conjunction with the appended drawing figures.

BRIEF DESCRIPTION OF THE DRAWINGS

FIG. 1 shows a top view of the resector and guide/rod disclosed in the parent application as mounted on the distal femur.

FIG. 2 shows a sagittal view of the resector and guide/rod of FIG. 1 as installed on the distal femur.

FIG. 3 shows a top view of the resector shown in FIGS. 1 and 2.

FIG. 4 shows a frontal view of the resector demonstrating the intercondylar notch pin of the resector of FIGS. 1-3.

FIG. 5 shows a perspective view of the distal femur showing the filed plane on the anterior femoral cortex thereof which receives the resector shown in FIGS. 1-4.

FIG. 6 is a side view of the femoral alignment guide/rod disclosed in the parent application.

FIG. 7 is a front view of the femoral alignment guide/rod shown in FIG. 6.

FIG. 8 shows a top view of the improved resector in accordance with the teachings of the present invention.

FIG. 9 shows a cross-sectional view along the line 9—9 of FIG. 8.

FIG. 10 shows a portion of the front of the improved resector demonstrating the open slot illustrated in FIGS. 8 and 9.

FIG. 11 shows a top view of a portion of a resector in accordance with the teachings of the parent application and the present application, with the improved femoral alignment guide/rod mounted thereon.

FIG. 12 shows a side view of the structure shown in FIG. 11.

FIG. 13 shows a front view of the femoral alignment guide/rod per se.

FIG. 14 shows a side view of an intramedullary rod.

SPECIFIC DESCRIPTION OF THE PREFERRED EMBODIMENTS

Hereinbelow, the specific description of FIGS. 1-7 is taken from the description thereof as set forth in parent application Ser. No. 888,525, filed July 23, 1986.

Reference is first made to FIG. 5 which shows in perspective view the distal portion of a femur 10. As shown, the distal femur has been filed on the anterior femoral cortex thereof to form a flat plane 11 on which is to be mounted the distal femoral resector 20. Also seen in FIG. 5 is a distal surface 13 of the femur 10 which is created by slicing off the distal end 15 of the femur 10. It should be understood that the distal end 15 of the femur 10 is sliced off the femur during the performance of the methods disclosed hereinafter which are accomplished through the use of the distal femoral resectors and femoral alignment guide/rods which are disclosed herein.

With particular reference, now, to FIGS. 1-4, it is seen that the distal femoral resector 20 includes a T-shaped housing 21 with the top 23 of the "T" having formed therethrough a slot 25 for a purpose to be described in greater detail hereinafter.

The leg 27 of the "T" has extending therethrough in a direction substantially parallel to the direction of the elongation of the top of the "T", a rotating rod 29 having a plurality of pin receiving holes 31, 33, 35 and 37 extending therethrough. In the preferred embodiment, the rotating rod 29 may rotate with respect to the leg 27 of the "T", an angular distance of approximately 30° to either side of a position of the holes 31, 33, 35 and 37 wherein they are parallel to the direction of penetration of the slot 25 into the top of the "T" 23.

As may be seen in FIGS. 1 and 2, some or all of the holes in the rotating rod 29 may have extending therethrough pins 39 which pin the rotating rod 29 and thereby the housing 21 to the distal femur.

The rotating rod 29 is rotatable as a safety feature so as to make sure that the surface 11 which has been filed on the anterior femoral cortex is engaged in a flush manner by the bottom surface 41 of the leg of the "T." As seen in FIGS. 2 and 3, at the proximal end 43 of the leg 27 of the "T", a further opening 45 is formed through which is adapted to be inserted a further pin 47 to further fixate the housing 21 on the distal femur.

With reference now to FIGS. 2, 3 and 4, it is seen that mounted at the distal end of the housing 21 on a distal wall 49 of the top of the "T", is a sliding intercondylar notch pin 50. As may be seen in FIG. 4, the notch pin 50 includes a T-shaped configuration with the top of the "T" 51 having a laterally elongated slot 53 through which are inserted two pins 55. Two pins 55 are used so as to constrain the lateral movements of the notch pin 50 to linear movements along the lateral extent of the elongated slot 53. The pins 55 have stems 57 which are frictionally retained within openings (not shown) in the distal wall 49 of the top of the "T" 23 of the housing 21 of the resector 20. The length of the stems 57 is chosen so that the undersides of the heads 59 of the pins 55 will frictionally engage the distal surface 61 of the top of the "T" 51 of the notch pin 50 so that slight pressure is necessary to laterally move the notch pin 50, however, the frictional forces are quite slight and movements of the resector 20 on the anterior femoral cortex will provide sufficient force application to the notch pin 50 to enable it to slide with respect to the fixed pins 55 to thereby enable its adjustment with respect to the intercondylar notch of the distal femur.

Depending downwardly from the top of the "T" 51, of the notch pin 51, is a pin member 63 which includes an angled portion 65 slightly angling in the proximal direction and a vertically depending portion 67 which is designed to fit into the intercondylar notch.

With reference, now, to FIGS. 1, 2, 6 and 7, it is seen that the femoral alignment guide/rod 70 includes a proximal rod 71 comprising a guiding element having connected at its distal end a hinge 73, 75 with the hinge portion 73 being integrally attached to the rod 71 and with the hinge portion 75 being attached to a rod aligning portion 77 thereof consisting of a rectangular cubic portion 79 having depending therefrom an elongated flat plate 81 sized and configured to fit precisely within the slot 25 of the resector housing 21. As should be understood, the pivoting motion of the rod 71 is constrained in a direction perpendicular to the direction of lateral elongation of the plate 81. Thus, when the plate 81 is inserted within the slot 25 of the resector housing 21, the pivoting of the rod 71 should be in a plane parallel to the direction of elongation of the leg 27 of the resector housing 21. Thus, with the plate 81 inserted into the slot 25 of the resector housing 21, the rod 71 may be pivoted to the position shown in FIG. 1 so that the alignment of the resector housing 21 as compared to the mechanical axis of the leg may be determined.

Thus, with the plate 81 inserted within the slot 25 of the resector housing 21, the direction of elongation of the rod 71 in the position shown in FIG. 1 may be compared with the mechanical axis of the leg and if there is misalignment, the resector housing 21 may be rotated or otherwise moved so as to ensure precise alignment of the rod 71 with the mechanical axis of the leg. When the rod 71 is aligned with the mechanical axis of the leg, the resector housing 21 will then be in perfect alignment at least laterally for the impending resection. Then, with such alignment existing, the resector housing 21 may be moved distally or proximally as may be the case so as to ensure lateral movements of the notch pin 50 until such time as the notch pin 50 properly seats in the intercondylar notch and the housing 21 is then perfectly aligned for the impending resection. At this point, pins such as those that are designated by the reference numeral 39 in FIGS. 1 and 2 may be driven through the rotating rod 29 with the resector housing 21 being adjusted through rotation of the rotating rod 29 with respect thereto so as to ensure that the bottom surface 41 of the leg 27 thereof is perfectly flush on the filed surface of the anterior femoral cortex designated by the reference numeral 11 in FIG. 5.

At this point, the rod 71 may be pivoted upwardly away from the femur so as to expose to the surgeon the opening 45 through the proximal end of the leg 27 of the resector housing 21. Thereafter, the pin 47 may be driven through the opening 45 and into the distal femur so as to securely fix the resector housing 21 thereon at at least three points, through the use of the pins 39 and 47.

FIGS. 1-7 having been described in the manner in which they were described in the parent application, the teachings of the present invention will be better understood.

With reference, first, to FIGS. 8, 9 and 10, the improved distal femoral resector designed to be used with an intramedullary technique.

In FIGS. 8-10, elements of like structure to the structure shown in FIGS. 1-7 will be referred to with like primed reference numerals. The improved resector 120 includes a T-shaped housing 21' with the top 23' of the "T" having formed therethrough a slot 25' for a purpose to be described in greater detail hereinafter. The leg 27' of the "T" has extending therethrough in a direction substantially parallel to the direction of elongation of the top of the "T", a rotating rod 29' having a plurality of pin receiving holes 31', 33', 35' and 37' extending therethrough. As is the case with the rotating rod 29 described with reference to FIGS. 1-7, the rotating rod 29' may rotate with respect to the leg 27' of the "T" an angular distance of approximately 30° to either side of a position of the holes 31', 33', 35' and 37' wherein they are parallel to the direction of penetration of the slot 25' into the top of the "T" 23'. In the same manner as shown in FIGS. 1 and 2, some or all of the holes in the rotating rod 29' may have extending therethrough pins which pin the rotating rod 29' and thereby the housing 21' to the distal femur on a planed surface such as that which is designated by the reference numeral 11 in FIG. 5. The operation of the rotating rod 29' is identical to the operation of the rotating rod 29 of the invention disclosed in FIGS. 1-7.

With further reference, in particular, to FIG. 8, it is seen that a further opening 45' is formed in the proximal end of the leg 27' of the "T" so that a further pin (not shown in FIGS. 8-10) may be inserted therethrough to further fixate the housing 21' on the distal femur.

With reference to FIG. 9, it is seen that the top 23' of the "T" has a distal face 122 to which is attached a housing 130 in any suitable manner such as, for example, the weld 124.

As seen in FIGS. 8-10, the housing 130 includes a double protractor scale 132, a block 134 including a threaded bore 136, and an open-ended slot 138 defined by downwardly depending legs 140, 142. The housing forms an interface between the resector body and intramedullary rod as will be described hereinafter.

As should be understood with reference to FIGS. 8 and 9, the double protractor scale 132 includes an upper protractor 144 and a lower protractor 146. With particular reference to FIGS. 8 and 9, it is seen that the upper protractor 144 includes a proximal stem 148 which is fixed to the distal face 122 of the top of the "T" 23' through the use of the weld 124. The upper protractor 144 has an opening 150 therethrough for a purpose to be described in greater detail hereinafter.

With further reference to FIGS. 8-10, it is seen that the lower protractor 146 has an opening 152 therethrough which may be aligned with the opening 150 in the upper protractor 144 to allow a bolt 160 having a head 162 and a threaded stem 164 to pass through the openings 150 and 152.

With particular reference to FIG. 9, it is seen that the block 134 is fixedly attached to the undersurface 166 of the lower protractor 146 by suitable means such as the weld 168. The threaded bore 136 of the block 134 is seen to be aligned with the bore 152 through the lower protractor 146 as the block 134 is welded to the lower protractor 146. The threads on the stem 164 of the bolt 160 are complimentary to the threads 136 to permit the assembly seen in FIGS. 8 and 9 in particular. Thus, it should be understood that the upper protractor 144 is constrained to move with the housing 21' whereas the lower protractor 146 is constrained to move with the block 134.

With reference to FIG. 14, an intramedullary rod 170 is seen to include a head 172 and an elongated rod portion 174 having outer dimensions designed to allow a close fit with the lateral dimensions of the slot 138 of the block 134 for a purpose to be described in greater detail hereinafter.

With further reference to FIGS. 8 and 9, it is seen that proximally of the rotating rod 29', a fixed pin 154 is installed in the leg 27' of the housing 21', which pin 154 includes protruding lateral portions 158 and 158 which protrude parallel to the lateral extent of the rotating rod 29' but which only extend a small portion of the distance of extension of the lateral sides of the rotating rod 29'. The pin 154 is provided for a purpose to be described in greater detail hereinafter.

In the use of the improved resector 120 shown in FIGS. 8-10, the surgeon must first take an X-ray from above the femur of the entire femur so that measurement may be made of the angle between the mechanical axis of the femur and the intramedullary canal thereof. As should be understood, the mechanical axis of the femur is a line extending between the intercondylar notch and the center of the femoral head. The intramedullary canal of the femur is the canal wherein marrow is contained. In the typical patient, this angle is approximately 6°, although angles of between 1° and 11° may be found. In this regard, the upper protractor 144 has a scale 145 and the lower protractor 146 has a scale 147, each of which allows a correction of from 0° to 11° with respect to the axis 123 of the housing 21'.

With the above discussed X-ray having been taken and the angle between the intramedullary canal and the mechanical axis of the femur having been measured, the bolt 160 is loosened to allow relative movement between the upper protractor 144 and the lower protractor 146. The angle between the mechanical axis of the femur and the intramedullary canal thereof may be dialed into the protractors by lining up the corresponding numbers on the upper and lower protractors. The indicia L and R on the upper protractor 144 designate left-hand and right-hand correction, depending on which femur is the subject of the operation. For example, to provide a 7° correction in the left-hand direction, the left-hand 7 on the protractor 144 is aligned with the left-hand 7 on the protractor 146. The protractors may be adjusted not only for the specific angle which is determined between the longitudinal extent of the intramedullary canal and the mechanical axis of the femur, but may also be adjusted to compensate for other anatomical variations, for example, to perform a valgus correction when the patient is "knock-kneed."

Going back to the example discussed hereinabove with the left-hand 7 of the protractor 144 lined up with the left-hand 7 of the protractor 146, the bolt 160 is tightened to fix the relative position of the protractors 144 and 146 and thereby the relationship between the slot 138 and the longitudinal extent of the housing 21'.

With reference, back, to FIG. 5, the point 14 is illustrated. An opening is formed through the surface 13 at the location of the point 14 which is midway between the condyles of the distal femur in the condylar notch. The hole is sufficiently large enough to allow insertion of the intramedullary rod 170 shaft 174. The shaft 174 is inserted into the intramedullary canal as far as it will go based upon the specific anatomy of the canal including its degree of bow. With the rod 174 having been so inserted, the housing 21' is placed on the surface 11 which has been planed onto the distal femur with the slot 138 sliding over the external dimensions of the rod 174 to fix the alignment of the housing 21' along the mechanical axis of the leg. The resector is then moved proximally until the proximal face of the block 134, with the slot 138 sliding on the rod 174, engages the intercondylar notch to properly position the cutting guide slot 25' in the proximal-distal direction. The resector housing 21' may be fixed in position by pins driven through the holes 31', 33', 35', 37', 45', as described hereinabove. Thereafter, if desired, the accuracy of the installation of the housing 21' may be checked through the use of the femoral alignment guide/rod 70, best seen in FIGS. 1, 2, and 6, as described hereinabove in the portion of the specification which has been incorporated from the parent application.

With reference to FIGS. 11, 12 and 13, an alternative femoral alignment guide/rod may be utilized with the resector described in FIGS. 1-7 or with the resector described with reference to FIGS. 8-10. In FIGS. 11 and 12, a resector 220 is illustrated with the top of the "T" and portions distal thereof being omitted to ensure understanding that the guide/rod described therein may be utilized with either the resector 20 or the resector 120. The resector 220 shown in FIGS. 11 and 12 includes the leg 227, the rotating rod 229 with holes 231, 233, 235 and 237 extending therethrough and with the leg 227 including the proximal hole 245 extending therethrough. A rod 254 is also provided which corresponds to the rod 154 best seen in FIGS. 8 and 9 and which includes laterally protruding portions 258. A femoral alignment guide/rod 300 is seen to include a rod aligning portion 301 and an elongated rod 303. The rod 303 is secured in a blind bore 305 formed at a proximal end of the rod aligning portion 301.

As best seen in FIGS. 12 and 13, the rod aligning portion 301 includes a rod attachment portion 307 at the proximal end which includes the blind bore 305 and, depending therefrom, an inverted U-shaped portion 309 having two legs 311 and 313. Each of the legs 311, 313 has a distal elongated slot 315 with the space 317 between the legs 311 and 313 being sized to allow secure sliding engagement on lateral walls 236, 238 of the leg 227. The slots 315 are sized to allow them to be snugly slid over the laterally depending portions 258 of the rod 254, with the length of the slots 315 being sized to allow rotation of the portion 307 of the guide/rod 300 with respect to the rod 254 with the portions 258 of the rod 254 being contained at their deepest possible penetration into the slots 315, with such rotation not resulting in any engagement with the rotating rod 229 due to the provision of curved surfaces 319, 321 formed on the distal end of the portion 307. In the use of the femoral alignment guide/rod 300, it is mounted on the proximal end of the leg 227 of the resector 220 in the manner seen in FIGS. 11 and 12 and is pivoted to the solid line position seen in FIG. 12 so that the proximal end of the rod 303 extends over the area of the femoral head of the femur to facilitate determination of alignment of the resector 220 with the mechanical axis of the leg. Again, it is stressed that the guide/rod 300 may be used with either the embodiment of resector 20 illustrated in FIGS. 1-7 or the resector 120 illustrated in FIGS. 8-10. The only modification which must be made to the resector 20 to facilitate the use of the guide/rod 300 is the addition of a pin corresponding to the pin 154 or 254.

The provision of the guide/rod 300 used in place of the guide/rod 70 is a significant advance. As should be understood with reference to FIGS. 1-7, when the guide/rod 70 is being employed, the slot 25 of the resector 20 must be used as the location of insertion of the plate 81 of the rod aligning portion 77. Thus, viewing the femur through the slot 25 is rendered impossible during the alignment phase of the operation. Furthermore, as should be understood from FIG. 1 in particular, when the guide/rod 70 is being employed, the rod 71 thereof overlies the leg 27 and central portions of the rotating rod 29. This makes it difficult to drive pins through the holes 31, 33, 35 and 37 of the rotating rod 29 and requires pivoting of the guide/rod 70 away from its overlying relation to the femoral head to facilitate driving of a pin through the hole 45 in the leg 27.

In contrast to this situation, with reference to FIGS. 11, 12 and 13, it should be clearly understood that the guide/rod 300 is entirely proximal of the rotating rod 229 and the slot 25, 25' of the resector on which it is installed. In addition, the cutting slot designated by the reference numeral 25 in FIGS. 1-7 and by the reference numeral 25' in FIGS. 8-10 is completely unobstructed allowing the surgeon to view therethrough the exact position on the distal femur where the cut is to take place.

In the embodiment of FIGS. 1-7, the guide/rod 300 may be employed by merely adding a pin corresponding to the pin 154 seen in FIGS. 8 and 9 and the pin 254 seen in FIGS. 11 and 12. If the guide/rod 300 is to be used in accordance with the teachings of FIGS. 1-7, then the guide/rod 300 in such circumstance would be the primary means of determining proper alignment of the resector 20 with respect to the mechanical axis of the associated femur. In the case of the embodiment of FIGS. 8-10, the guide/rod 300 may be employed merely to check the accuracy of alignment of the resector 120 which has been accomplished through the use of the intramedullary technique described hereinabove. Use of the extramedullary guide/rod 300 in conjunction with use of the resector 120 illustrated in FIGS. 8-10 is optional, however, such use is recommended if there is an anatomical bow of the femur that will not allow proper insertion of the intramedullary guide/rod 170.

With the structure disclosed in FIGS. 8-14 having been described in great detail, now, the specific method of performing surgery using the instruments described therein will be made.

(a) As seen in FIG. 5, the distal femur is prepared for the attachment of the resector through the filing of the anterior femoral cortex to form the surface 11.

(b) Either before or after the step described in paragraph (a) above, the entirety of the femur is X-rayed from above in a position wherein the femoral head extends laterally in the view (anterior-posterior view).

(c) From this X-ray, the angular relationship between the longitudinal extent of the intramedullary canal and a line between the intercondylar notch and the femoral head which defines the mechanical axis of the leg may be determined.

(d) With the angle between the longitudinal extent of the intramedullary canal and the mechanical axis of the leg having been determined, this angular relationship is dialed into the gauge 132 with provision being made, where desired, for any additional corrections such as, for example, in the case of the desirability of a valgus correction.

(e) A hole is formed through the intercondylar notch at the point referred to with reference numeral 14 in FIG. 5. The hole extends completely through the face of the intercondylar notch so as to enable gaining of access to the intramedullary canal (not shown).

(f) The intramedullary rod 170 rod portion 174 is then inserted through the opening 14 and into the intramedullary canal as far as the rod will go in the proximal direction. It should be understood that the natural bowing of the intramedullary canal will cause the end of the rod portion 174 to engage the interior wall of the intramedullary canal in some cases after the rod portion 174 has been inserted into the intramedullary canal a sufficient distance in the proximal direction. The rod portion 174 of the intramedullary rod 170 is made sufficiently long enough so that if the end of the rod is not centrally located within the intramedullary canal but is, rather, offset to one side or another within the canal, the maximum error in orientation of the intramedullary rod will not exceed approximately $\frac{1}{4}$°.

(g) With the intramedullary rod 170 having been inserted into the intramedullary canal as far as it will go, the resector 120 is placed on the filed surface 11 of the distal femur with the slot 138 slidably placed over the rod portion 174 of the intramedullary rod 170.

(h) With such placement having been carried out, the resector is pushed firmly against the intercondylar notch and pins are placed through the openings in the rotating rod 29' and the floating interaction between the rotating rod 29' and the resector housing 21' is used to firmly mount the resector housing 21' flush on the surface 11 which has been filed onto the anterior femoral cortex.

(i) Thereafter, additional pins may be used extending through the hole 45' as well as the other holes in the rotating rod 29' to firmly fixate the resector 120 in mounted position on the distal femur.

(j) With the resector so mounted, the accuracy of its mounted position may be verified through the use of either the guide/rod 70 or the guide/rod 300 in the manner described hereinabove. Of course, use of the guide/rod 300 is preferred because this allows viewing through the slot 25' of the area on the distal femur where resection is to take place. Furthermore, if adjustment is to take place in the distal femur where pins have been driven, complete access is available to each of the holes 31', 33', 35', 37' and 45' so that corrections in placement may easily be made. Such verification may be undertaken, if desired, prior to any pin insertion.

(k) Thereafter, resection of the distal femur is assured to be 90° to the filed surface of the anterior femoral cortex 11.

With the preferred method of operation of the embodiment of FIGS. 8-10 having been described in conjunction with the guide/rod 70 or 300, it is believed instructive to set forth calculations which demonstrate the great accuracy of resection of the distal femur which may be accomplished through the use of the resector 120 when used with the intramedullary technique including the use of the intramedullary rod 170.

Firstly, it should be understood that many surgical techniques measure the resection off a deformed medial femoral condyle. When measurements are taken from a position offset from the center of the knee, large errors are quite possible.

In the teachings of the present invention through the use of the centralized intramedullary rod, such errors are absolutely minimized. When the rod is inserted through the opening at 14 (FIG. 5) through the center of the intercondylar notch, in theory, the rod may pivot about the point 14 to the extent limited by the width of the intramedullary canal where the end of the rod, typically 10 inches in length, is located. This error rarely exceeds 0.470 inches or 3°. However, the alignment slot 138 of the intercondylar pin 134 extends distally from point 14 only 0.625 of an inch, translating to an approximate error of only 0.2° from optimum alignment of the resector on the rod.

As should be understood by those skilled in the art, this cutting error is insignificant and virtually immeasurable. These results accrue due to the fact that the present invention uses the anatomical landmark of the center of the intercondylar notch as the point about which all measurements and calculations are taken.

As such, an invention has been described in terms of preferred embodiments thereof which fulfill each and every one of the objects of the invention as set forth hereinabove and provide a new and improved distal femoral resector and method of operating in conjunction therewith which is far superior to other known instruments and procedures including those which are disclosed in the parent application.

Of course, various changes, modifications and alterations may be made in the teachings of the present invention without departing from the intended spirit and scope thereof. As such, it is intended that the present invention only be limited by the terms of the appended claims.

I claim:

1. In a distal femoral resector for use in resecting the distal femur of a leg, said distal femur having a substantially flat surface formed on the anterior femoral cortex thereof, said resector comprising a base of substantially T-shaped configuration and adapted to be placed in overlying relation to said substantially flat surface, said substantially T-shaped configuration being defined by a proximal leg portion and a distal transverse portion, a rotating rod rotatably mounted through said leg portion and including means for attaching said base to said distal femur, said rod being rotatable to facilitate firm and flush attachment of said base to said substantially flat surface, an intercondylar notch pin attached to a distal side of said transverse portion; the improvement comprising:
   (a) an attachment member on said proximal leg portion proximal of said rotating rod; and
   (b) means for aligning said resector removably attachable to said attachment member.

2. The invention of claim 1, wherein said attachment member comprises an attachment rod extending substantially parallel to said rotating rod.

3. The invention of claim 1, wherein said means for aligning said resector comprises an aligning portion and an elongated rod attached to said aligning portion, said aligning portion including structure allowing removable attachment to said attachment member.

4. The invention of claim 2, wherein said means for aligning said resector comprises an aligning portion and an elongated rod attached to said aligning portion, said aligning portion including structure allowing removable attachment to said attachment member.

5. The invention of claim 4, wherein said structure allowing removable attachment comprises a pair of spaced legs each having an elongated open slot therein, each said slot being adapted to be mounted over a respective end of said attachment rod, and when so mounted allowing rotation of said means for aligning about an axis defining the direction of elongation of said attachment rod.

6. In a distal femoral resector for use in resecting the distal femur of a leg, said distal femur having a substantially flat surface formed on the anterior femoral cortex thereof, said resector comprising a base of substantially T-shaped configuration and adapted to be placed in overlying relation to said substantially flat surface, said substantially T-shaped configuration being defined by a substantially T-shaped configuration being defined by a proximal leg portion and a distal transverse portion, a rotating rod rotatably mounted through said leg portion and including means for attaching said base to said distal femur, said rod being rotatable to facilitate firm and flush attachment of said base to said substantially flat surface, the improvement comprising:
   (a) an attachment member on said proximal leg portion proximal of said rotating rod; and
   (b) means for aligning said resector removably attachable to said attachment member.

7. The invention of claim 6, wherein said attachment member comprises an attachment rod extending substantially parallel to said rotating rod.

8. The invention of claim 6, wherein said means for aligning said resector comprises an aligning portion and an elongated rod attached to said aligning portion, said aligning portion including structure allowing removable attachment to said attachment member.

9. The invention of claim 7, wherein said means for aligning said resector comprises an aligning portion and an elongated rod attached to said aligning portion, said aligning portion including structure allowing removable attachment to said attachment member.

10. The invention of claim 9, wherein said structure allowing removable attachment comprises a pair of spaced legs each having an elongated open slot therein, each said slot being adapted to be mounted over a respective end of said attachment rod, and when so mounted allowing rotation of said means for aligning about an axis defining the direction of elongation of said attachment rod.

11. The invention of claim 6, further including intramedullary means for aligning said resector on said surface.

12. The invention of claim 11, wherein said intramedullary means comprises:
   (a) an elongated rod inserted into the intramedullary canal of said femur through an opening formed though the intercondylar notch thereof with a distal end of said elongated rod protruding distally of said opening;
   (b) an adjustable interface between said elongated rod and said resector base, said interface being adjustable to establish a predetermined angular relationship between the longitudinal extent of said resector proximal leg portion and the longitudinal extent of said elongated rod.

13. The invention of claim 12, wherein said resector proximal leg portion is placed on said flat surface in alignment with the mechanical axis of said leg, said interface being adjustable to align said resector proximal leg portion with said leg mechanical axis.

14. The invention of claim 12, wherein said interface comprises:
   (a) a housing attached to a distal face of said distal transverse portion;
   (b) a first protractor fixedly attached to said housing;
   (c) a block including an open ended slot placeable over said elongated rod distal end;
   (d) a second protractor fixedly attached to said block;
   (e) said housing and block being pivotably mounted together at respective centers of said protractors;
   (f) each said protractor having a degree scale thereon, said scales having respective markings thereon which may be aligned to define particular angular relationships between said slot and said distal face; and (g) means for selectively locking said protractors at any of said particular angular relationships.

15. The invention of claim 1, wherein said distal transverse portion includes an elongated slot extending therethrough and adapted to receive therethrough means for resecting said distal femur, said slot being operative to guide said means for resecting.

16. The invention of claim 6, wherein said distal transverse portion includes an elongated slot extending therethrough and adapted to receive therethrough means for resecting said distal femur, said slot being operative to guide said means for resecting.

17. The invention of claim 14, wherein said scales have respective markings defining angular relationships of from 0° to 11° for left and right femurs.

18. A method of resecting the distal femur of a leg, including the steps of:
 (a) filing a substantially flat surface on the anterior femoral cortex;
 (b) placing the base of a distal femoral resector on said surface;
 (c) said resector including a guide slot extending therethrough for guiding a cutting tool in resecting said distal femur;
 (d) aligning said resector with the mechanical axis of said leg using intramedullary alignment means;
 (e) firmly fixing said base to said surface; and
 (f) resecting said distal femur.

19. The method of claim 18, wherein said base includes a rotating rod including means thereon for fixing said base to said surface, and said placing step further including the step of initially fixing said rotating rod to said surface with the rotating rod being rotatable to align said base to said surface, said firmly fixing step including the step of fixing said base to said surface with fixation means extending through said base.

20. A method of resecting the distal femur of a leg, including the steps of:
 (a) filing a substantially flat surface on the anterior femoral cortex;
 (b) placing the base of a distal femoral resector on said surface;
 (c) said resector including a guide slot extending therethrough for guiding a cutting tool in resecting said distal femur;
 (d) aligning said resector with the mechanical axis of said leg using alignment means attachable to a proximal end of said base;
 (e) firmly fixing said base to said surface; and
 (f) resecting said distal femur.

21. A method of resecting the distal femur of a leg, including the steps of:
 (a) placing the base of a distal femoral resector on a flattened surface formed on said distal femur substantially parallel to the anatomical bow of said femur;
 (b) said resector including an intercondylar notch pin, said method further including the step of adjusting the depth of resection by locating said notch pin into the anatomical intercondylar notch of said femur;
 (c) said resector including a cutting guide slot, said method further including the step of attaching an alignment device having a pivoting guide rod to said resector by inserting a guide plate of said alignment device into said slot;
 (d) pivoting said guide rod to a first position allowing alignment of said resector with the mechanical axis of the leg and so aligning said resector;
 (e) pivoting said guide rod to a second position allowing firm fixation of said base to said surface and firmly fixing said base to said surface;
 (f) removing said guide plate from said slot;
 (g) resecting said distal femur by inserting a cutting tool through said slot.

22. The method of claim 21, wherein said resector base has a rotating rod attached thereto, said firmly fixing step including the step of allowing said base to rotate with respect to said rotating rod to allow said base to sit flat on said surface and driving pins into said femur through holes formed through said rotating rod.

23. The method of claim 18, wherein said intramedullary alignment means comprises;
 (a) an intramedullary rod;
 (b) an adjustable interface on said base including attachment means for allowing removable attachment of said interface on said rod, said interface being adjustable to adjust the angular relationship between said rod and the longitudinal extent of said base; said alignment step including the steps of:
   (1) forming an opening through the intercondylar notch of said femur;
   (2) inserting said rod into the intramedullary canal of said femur through said opening, leaving a distal end of said rod protruding distally of said opening;
   (3) adjusting said interface to provide a predetermined said angular relationship; and
   (4) placing said base on said distal femur with said attachment means on said rod.

24. The method of claim 23, further including the step of checking alignment of said resector with the mechanical axis of said leg by attaching a pivotable guide rod to a proximal end of said base.

25. A method of resecting the distal femur of a leg, including the steps of:
 (a) measuring the angular relationship between the longitudinal axis of the intramedullary canal of said femur and the mechanical axis of said leg;
 (b) providing a distal femoral resector including a base and an interface, said resector including adjustment means for adjusting the angular relationship between the longitudinal extent of said base and said interface;
 (c) adjusting said adjustment means to establish said angular relation between the longitudinal extent of said base and said interface;
 (d) forming a hole through the intercondylar notch of said femur;
 (e) inserting an intramedullary rod into said intramedullary canal through said hole, leaving the distal end of said rod protruding distally of said hole;
 (f) placing said resector on a previously formed substantially flat surface on the anterior femoral cortex with said interface placed over said rod distal end and a proximal face of said interface engaging said intercondylar notch to cause said base to be aligned in predetermined relationship with said mechanical axis of said leg;
 (g) firmly fixing said base on said surface; and
 (h) resecting said distal femur.

26. The method of claim 25, wherein said measuring step is carried out by performing an X-ray of said leg.

27. The method of claim 25, wherein said adjusting step adjusts the angular relationship between the longitudinal extent of said base and said interface to compensate for a leg deformity.

28. The method of claim 25, wherein said interface includes a gauge including two relatively rotatable plates, each said plate having indicia thereon related to said angular relationship, said plates being adjustable to align respective indicia on respective ones of said plates with one another to establish said angular relation.

29. The method of claim 25, wherein said resector base has a rotating rod attached thereto, said firmly fixing step including the step of allowing said base to rotate with respect to said rotating rod to allow said base to sit flat on said surface and driving pins into said femur through holes formed through said rotating rod.

30. The method of claim 25, wherein said base includes a cutting guide slot, said resecting step including the step of inserting a cutting device through said slot.

31. The method of claim 29, further including the step of checking alignment of said resector on said surface after said firmly fixing step by attaching a pivotable guide rod to a proximal end of said base.

32. The method of claim 29, further including the step of checking alignment of said resector on said surface prior to said firmly fixing step by attaching a pivotable guide rod to a proximal end of said base.

* * * * *